United States Patent
Dalvi et al.

(10) Patent No.: US 9,986,952 B2
(45) Date of Patent: Jun. 5, 2018

(54) HEART SOUND SIMULATOR

(71) Applicant: Masimo Corporation, Irvine, CA (US)

(72) Inventors: Cristiano Dalvi, Lake Forest, CA (US); Marcelo M. Lamego, Cupertino, CA (US)

(73) Assignee: Masimo Corporation, Irvine, CA (US)

( * ) Notice: Subject to any disclaimer, the term of this patent is extended or adjusted under 35 U.S.C. 154(b) by 0 days. days.

(21) Appl. No.: 14/203,376

(22) Filed: Mar. 10, 2014

(65) Prior Publication Data
US 2014/0276115 A1    Sep. 18, 2014

Related U.S. Application Data

(60) Provisional application No. 61/782,374, filed on Mar. 14, 2013.

(51) Int. Cl.
*A61B 5/00* (2006.01)
*A61B 5/024* (2006.01)
*A61B 5/0402* (2006.01)
*A61B 5/1455* (2006.01)

(52) U.S. Cl.
CPC ............ *A61B 5/7415* (2013.01); *A61B 5/024* (2013.01); *A61B 5/02416* (2013.01); *A61B 5/7278* (2013.01); *A61B 5/04028* (2013.01); *A61B 5/14551* (2013.01); *A61B 5/7221* (2013.01)

(58) Field of Classification Search
CPC .................................................. A61B 5/7415
See application file for complete search history.

(56) References Cited

U.S. PATENT DOCUMENTS

| | | | |
|---|---|---|---|
| 3,399,467 A | * | 9/1968 | Abe ...................... G09B 23/28 434/266 |
| 4,653,498 A | * | 3/1987 | New, Jr. ............. A61B 5/14551 600/324 |
| 4,960,128 A | | 10/1990 | Gordon et al. |
| 4,964,408 A | | 10/1990 | Hink et al. |
| 5,041,187 A | | 8/1991 | Hink et al. |
| 5,069,213 A | | 12/1991 | Polczynski |
| 5,163,438 A | | 11/1992 | Gordon et al. |
| 5,319,355 A | | 6/1994 | Russek |
| 5,337,744 A | | 8/1994 | Branigan |
| 5,341,805 A | | 8/1994 | Stavridi et al. |

(Continued)

OTHER PUBLICATIONS

Oversampling by Wikipedia, the free encyclopedia, pub. online Oct. 7, 2012 at "https://en.wikipedia.org/w/index.php?title=Oversampling&oldid=516454012", accessed Sep. 3, 2015.*

(Continued)

*Primary Examiner* — Katherine Fernandez
*Assistant Examiner* — Michael Kellogg
(74) *Attorney, Agent, or Firm* — Knobbe Martens Olson & Bear LLP

(57) ABSTRACT

The disclosure includes systems and methods directed toward simulating heart sounds. The system can include an optical sensor configured to obtain data for generating a plurality of plethysmograph waveforms at a first frequency. The heart sound simulator can also include a processor in communication with the sensor. The processor can be configured to generate a heart sound signal based on at least one of the plurality of plethysmograph waveforms.

18 Claims, 9 Drawing Sheets

(56) References Cited

U.S. PATENT DOCUMENTS

| | | |
|---|---|---|
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,730,140 A * | 3/1998 | Fitch .................. A61B 5/0205 600/514 |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 * | 4/2003 | Al-Ali ................ A61B 5/02416 600/323 |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |

(56) References Cited

U.S. PATENT DOCUMENTS

| | | |
|---|---|---|
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |

(56) References Cited

U.S. PATENT DOCUMENTS

| | | | |
|---|---|---|---|
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2005/0065417 A1* | 3/2005 | Ali | A61B 5/0002 600/323 |
| 2008/0013747 A1* | 1/2008 | Tran | A61B 7/04 381/67 |
| 2011/0028802 A1* | 2/2011 | Addison | A61B 5/08 600/301 |
| 2011/0196211 A1* | 8/2011 | Al-Ali | A61B 5/14551 600/300 |

OTHER PUBLICATIONS

Pseudorandom noise by Wikipedia, the free encyclopedia, pub. online Jul. 25, 2012 at "https://en.wikipedia.org/w/index.php?title=Pseudorandom_noise&oldid=504121479"; accessed Sep. 3, 2015.*

Noise generator by Wikipedia, the free encyclopedia, pub. online May 6, 2012 at "https://en.wikipedia.org/w/index.php?title=Noise_generator&oldid=490897729"; accessed Sep. 3, 2015.*

* cited by examiner

HEART SOUND SIMULATOR

PRIORITY CLAIM AND REFERENCE TO RELATED APPLICATIONS

The present application claims priority benefit under 35 U.S.C. § 119(e) to U.S. Provisional Patent Application Ser. No. 61/782,374, filed Mar. 14, 2013, titled Heart Sound Simulator; hereby incorporated in its entirety by reference herein.

BACKGROUND

Field

The disclosure relates to systems and methods for simulating heart sounds.

Description of the Related Art

Clinicians commonly use stethoscopes to listen to sounds inside the body. For example, stethoscopes can be used to listen to lung sounds and heart sounds. Some stethoscopes can be used with a recording device to record the internal body sounds. However, these audio recordings can require large amounts of data storage.

Newer technologies provide for electronic patient monitoring using acoustic sensors. For example, Masimo Corporation of Irvine, Calif. commercially provides noninvasive and continuous monitoring of breathing, specifically the respiration rate using an adhesive sensor with an integrated acoustic transducer that is applied to the patient's neck. In some instruments, data from the acoustic sensor is used to drive an audio transducer such that the instrument reproduces audio the same as or very similar to the original sensed breathing. The data may be audibly presented substantially real time or stored for later playback. However, as with electronic stethoscopes, the recording of this data can require large amounts of data storage.

SUMMARY

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

One aspect of this disclosure is directed toward a heart sound simulator configured to determine heart sounds from photo-plethysmograph data. The heart sound simulator can include an optical sensor in communication with a processor. For example, the sensor can include a light source and a light detector and can be configured to output one or more sensor signals responsive to attenuation of light by body tissue. The processor can receive the at least one signal responsive to the sensor signal and can be configured to process the received signal to determine a plurality of plethysmograph waveforms and output a heart sound signal responsive to at least one of the plurality of plethysmograph waveforms. In some embodiments, the sensor may advantageously be a noninvasive sensor including one or more light sources and one or more light detectors positioned proximate patient tissue at a measurement site by a sensor housing or positioning member such as adhesive tape. The detector(s) may advantageously detect light attenuated by pulsing blood. In some embodiments, the sensor may include active pulsing technologies designed to move tissue near a measurement site in a predetermined manner at a predetermined frequency. In an embodiment, the sensor comprises an oximetry sensor.

In the above mentioned aspect, the processor can be further configured to use calibration information to determine the heart sound signal.

In any of the above mentioned aspects, the processor can be further configured to oversample the at least one plethysmograph waveform. The plethysmograph waveforms can include a first frequency and the processor can be configured to oversample the at least one plethysmograph waveform at a second frequency greater than the first frequency. In some embodiments, the second frequency is substantially greater, and, in certain embodiments, the second frequency is at least about 100 times the first frequency.

In any of the above mentioned aspects, the heart sound simulator can include a noise generator configured to generate pseudo-random noise. The heart sound simulator can also include a filter configured to filter the pseudo-random noise for one or more heart tones.

In any of the above mentioned aspects, the processor can be further configured to output the heart sound signal in an audio format.

In any of the above mentioned aspects, the processor can receive the at least one signal or the plurality of plethysmograph waveforms from a memory storing trends of the at least one signal or the plurality of plethysmograph waveforms. The at least one signal or the plurality of plethysmograph waveforms can correspond to a caregiver-selected time window from said trends. The time window can surround one or more abnormal values in measurement data. The abnormal values can be determined proximate a time when said processor received said at least one signal from said sensor.

Another aspect of this disclosure is directed toward a method of simulating heart sounds using one or more plethysmograph signals responsive to light attenuated by body tissue detected by an optical sensor in proximity to a measurement site. The method can include receiving signals responsive to light attenuated by body tissue. The method can include electronically identifying a plurality of plethysmograph waveforms using a signal processor, electronically selecting at least one plethysmograph waveform using the signal processor, and electronically generating a heart sound signal based on the at least one plethysmograph waveform. The method may also include creating audible heart sounds through a transducer responsive to the heart sound signal.

In the above mentioned method aspect, identifying the plurality of plethysmograph waveforms can include electronically sampling a plurality of signal streams at a first frequency. The method can also include electronically oversampling the at least one plethysmograph waveform at a second frequency higher than the first frequency.

In any of the above mentioned method aspects, the method can include electronically generating pseudo-random noise. The method can also include electronically filtering the pseudo-random noise for one or more natural heart tones.

In any of the above mentioned method aspects, the method can also include electronically transforming the at least one plethysmograph waveform using a heart sound model.

In any of the above mentioned method aspects, the method can also include electronically outputting the heart sound signal in an audio format.

Yet another aspect of this disclosure is directed toward a non-transitory computer storage having stored thereon a system configured to execute in one or more processors. The system can include a calibration module configured to select at least one plethysmograph waveform. The system can also include a plethysmograph processing module configured to generate a heart sound signal based on the at least one plethysmograph waveform.

In the above mentioned non-transitory computer storage aspect, the calibration module can be configured to select the at least one plethysmograph waveform using calibration information based at least in part on parameters associated with creating an audio output and/or physiological data.

In any of the above mentioned non-transitory computer storage aspects, the plethysmograph processing module can be configured to transform the at least one plethysmograph waveform using a heart sound model.

Yet another aspect of this disclosure is directed toward a method of producing clinically relevant information different from stored trend data. The method can include acquiring the trend data, which can include one or more of an input signal, plethysmograph, or measurement data. The input signal can be, for example, responsive to light attenuated by body tissue. The method can also include selecting a time window in the trend data and producing data different from the trend data. In certain aspects, the produced data can have a higher frequency than the stored data.

In the above mentioned method of producing clinically relevant information, the clinically relevant information can include heart sounds and/or an EKG output, which can be synchronized with each other and/or to a plethysmograph.

In any of the above mentioned methods of producing clinically relevant information, selecting the time window can be automatic or carried out by a caregiver based on one or more abnormalities in the trend data, including, but not limited to, abnormalities in the measurement data.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

DETAILED DESCRIPTION

Pulse oximeter systems are commonly used to noninvasively measure physiological data. In general, a pulse oximeter system includes one or more optical sensors communicating with a processing instrument to display the noninvasively measured values. The sensor includes a light source that irradiates tissue of a patient and one or more photodetectors that detect the radiation after attenuation thereof by the tissue. The sensor communicates the detected signal(s) to the processing instrument, or patient monitor, where the instrument often removes noise from and otherwise preprocesses the received signal(s). The instrument then processes the signal(s) to determine measurement values for one or more monitored parameters or combinations thereof. The patient monitor may numerically or graphically display various measurement values of physiological parameters, combinations of measurement values, or graphical representations of the same. In some embodiments, the graphical representation may include analog-appearing representations. In other embodiment, the graphical representation may include, but is not limited to, the patient's plethysmograph, which is a visual display of the patient's pulse contour and pulse rate. The instrument may display a myriad of other calculated measurements of other physiological parameters.

Figure 1:
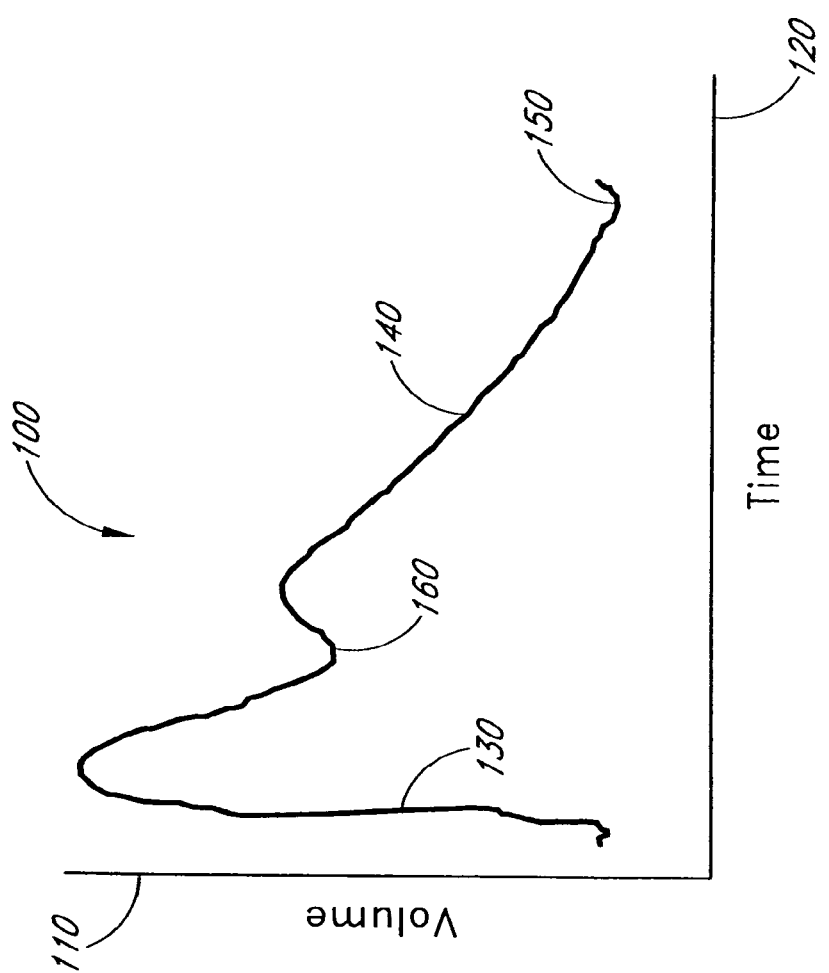
FIG. 1 is a graph illustrating a standard plethysmograph waveform.

FIG. 1 illustrates the standard plethysmograph waveform 100, which can be electronically derived using a pulse oximeter. The waveform 100 is a display of blood volume, shown along the y-axis 110, over time, shown along the x-axis 120. The shape of the plethysmograph waveform 100 is a function of heart stroke volume, pressure gradient, arterial elasticity, and peripheral resistance. The ideal waveform 100 displays a broad peripheral flow curve, with a short, steep inflow phase 130 followed by a 3 to 4 times longer outflow phase 140. The inflow phase 130 is the result of tissue distention by the rapid blood volume inflow during ventricular systole. During the outflow phase 140, blood flow continues into the vascular bed during diastole. The end diastolic baseline 150 indicates the minimum basal tissue perfusion. During the outflow phase 140 is a dicrotic notch 160, the nature of which is disputed. Classically, the dicrotic notch 160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

Figure 2:
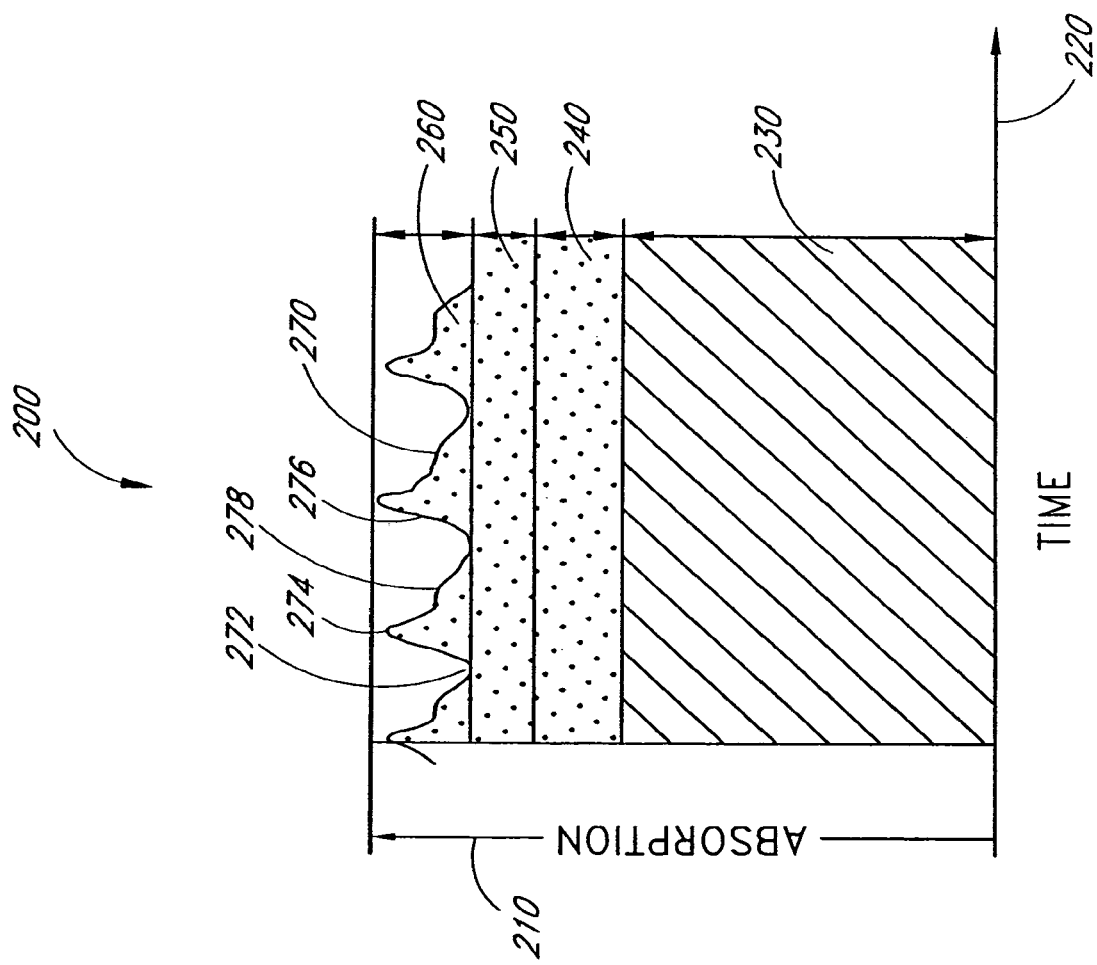
FIG. 2 is a graph illustrating the absorption contribution of various blood and tissue components.

FIG. 2 is a graph 200 illustrating a compartmental model of the absorption of light at a tissue site illuminated by a pulse oximetry sensor. The graph 200 has a y-axis 210 representing the total amount of light absorbed by the tissue site, with time shown along an x-axis 220. The total absorption is represented by layers, including the static absorption layers due to tissue 230, venous blood 240, and a baseline of arterial blood 250. Also shown is a variable absorption layer due to the pulse-added volume of arterial blood 260. The profile 270 of the pulse-added arterial blood 260 is seen as the plethysmograph waveform 100 depicted in FIG. 1.

Figure 3:
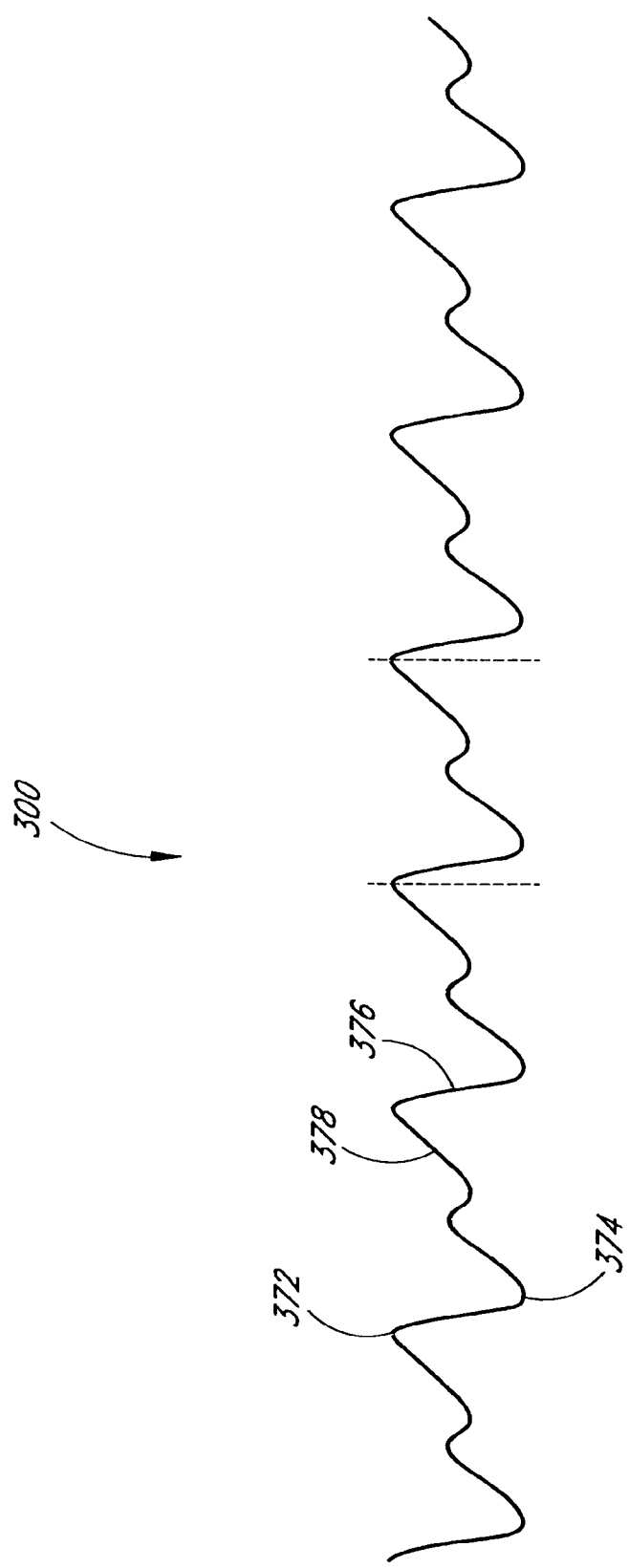
FIG. 3 is a graph illustrating an intensity "plethysmograph" pulse oximetry waveform.

FIG. 3 illustrates the photo-plethysmograph intensity signal 300 detected by a pulse oximeter sensor. A pulse oximeter does not directly detect the standard plethysmograph waveform 100 (FIG. 1). However, the standard plethysmograph can be derived by observing that the detected intensity signal 300 is merely an out of phase version of the absorption profile 270. That is, the peak detected intensity 372 occurs at minimum absorption 272 (FIG. 2), and the minimum detected intensity 374 occurs at maximum absorption 274 (FIG. 2). Further, a rapid rise in absorption 276 (FIG. 2) during the inflow phase of the plethysmograph is reflected in a rapid decline 376 in intensity, and the gradual decline 278 (FIG. 2) in absorption during the outflow phase of the plethysmograph is reflected in a gradual increase 378 in detected intensity.

Figure 4:
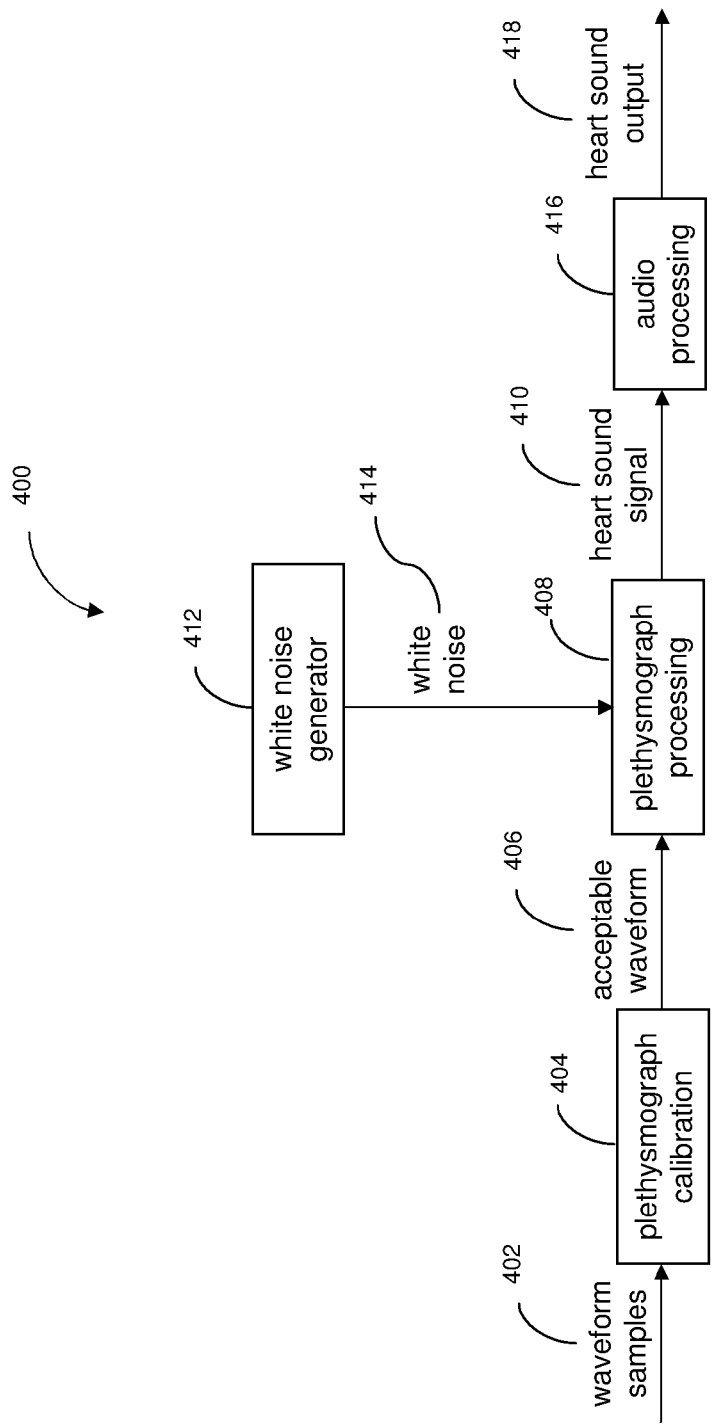
FIG. 4 is a block diagram of an exemplary data flow through one or more signal processors to simulate a heart sound using a plethysmograph waveform.
Figure 5:
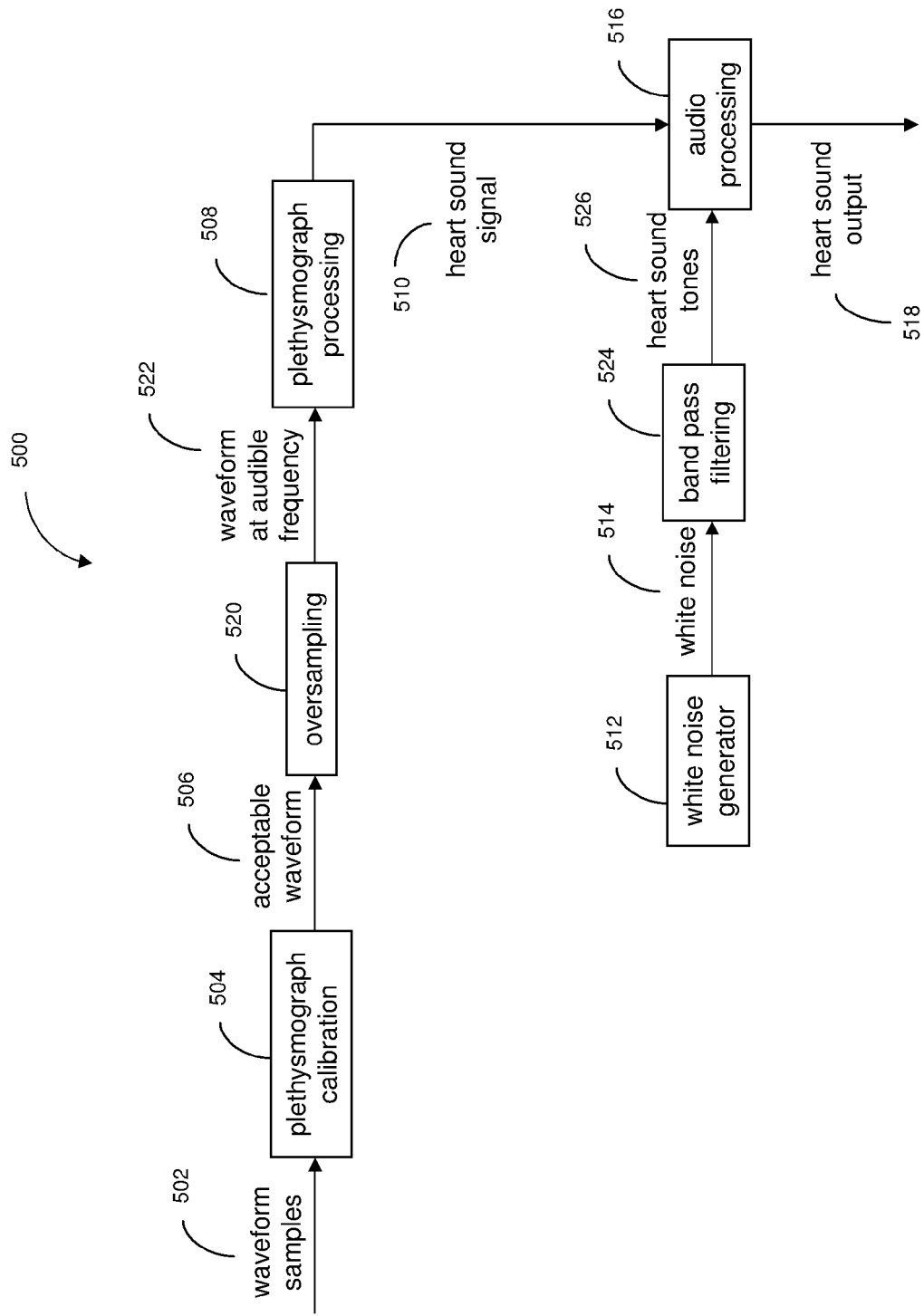
FIG. 5 is a block diagram of another exemplary data flow through one or more signal processors to simulate a heart sound using a plethysmograph waveform.

FIGS. 4 and 5 illustrate exemplary data flows as signals are processed by an instrument. An artisan will recognize that modern pulse oximetry instruments may include pre-processing circuitry to prepare incoming detector signals, one or more signal processors communicating with the preprocessing circuitry to receive the preprocessed detector signals and use a wide array of processing techniques to determine a wide array of measurement values for a wide array of physiological parameters. The signal processors and other processing devices can execute sophisticated software to accomplish processing modules provided herein and known to processing modules. The signal processors and other processing devices may include on-chip memory, may be operable communicating with memory, data storage devices or the like. In addition, one or more instrument processors may receive the measurement data from the signal processor(s) and govern the output and display of information to the user, the output and display being responsive to the data from the signals processor(s).

As shown in FIGS. 4, 4A, 5 and 5A, the data flows provide exemplary methods of processing data collected from an optical sensor to simulate sounds inside the body (e.g., lung sounds, heart sounds, stomach sounds, etc.) The methods can be carried out using a heart sound simulator system including a pulse oximeter in communication with a processor. The pulse oximeter can include a sensor configured to obtain data necessary to generate one or more plethysmographs, and the processor can carry out one or more of the steps described in connection with methods described herein. Other embodiments may use the processor of the pulse oximeter to simulate sounds inside the body.

Although heart sounds are used as an example throughout the specification, the methods disclosed herein can be used to convert the plethysmograph to sounds inside any other portion of the body. Further, as used herein, the term "plethysmograph" can refer to either the standard plethysmograph or the intensity plethysmograph.

When clinicians check on patients, the clinician may listen to the patient's heart sounds, which the clinician may or may not record. Beyond these periodic visits, clinicians do not have access to heart sounds at any other time intervals. The presently disclosed methods permit the clinician to listen to the patient's heart sounds at any time interval based on previously recorded plethysmographs. Thus, if, for example, the clinician notices or an instrument flags for the clinician abnormal changes in the patient's physiological state or trend (e.g. blood pressure, oxygen saturation, glucose levels, in the morphology of the plethysmograph, etc.), the clinician can listen to the patient's heart sounds from time periods around (before, during, and/or after) the abnormal change. These methods can also be useful for researchers to access patient data to study trends for a single patient or a patient population.

The exemplary methods disclosed herein also decrease the total amount of storage space necessary to store heart sound recordings. Audio recordings generally require a large amount of storage space relative to a plethysmograph. Recording internal body sounds from multiple parts of the body would require an even greater amount of storage space. Using the methods described herein, clinicians may advantageously store a single plethysmograph over time to convert the plethysmograph into one or more audio signals representative of different internal body sounds. In an embodiment, calibration data is also stored with the plethysmograph.

The ability to simulate different internal body sounds using a plethysmograph also decreases the number of cables connected to the patient. Ordinarily, to record sounds from different sections of the body, a cable or device would need to be connected to sensors proximate each of those body sections. The exemplary methods permit the clinician to obtain the recordings from the data already being acquired by the pulse oximeter. As the pulse oximeter is a standard of care instrument in caregiver environments, use of data already being acquired for new insight and information into a patient's condition is highly advantageous.

FIG. 4 illustrates an exemplary data flow 400 of processing the plethysmograph to simulate heart sounds. Generally, the data flow 400 can include calibrating plethysmograph samples 402 to select one or more acceptable plethysmograph waveforms 406 (block 404), and processing the one or more acceptable waveforms 408, alone or in combination with white noise 414, to create a heart sound signal 410 (block 408). Finally, the data flow can include converting the heart sound signal 410 to an audio heart sound output 418 (block 416), which could be an audio signal, an audible signal, or data file usable by another device to produce the any or all of the foregoing. The data flow illustrated in FIG. 4 advantageously reduces the computational processing, and thus processor usage and processing power consumption used converting the plethysmograph to an audio output.

The sample waveforms 402 generated by the pulse oximeter can include samples of one or more detected plethysmographs. For example, the pulse oximeter sensor can include a light source emitting two (2), eight (8), sixteen (16), or other number of differing wavelengths of light (e.g., 8 LEDs that emit different wavelengths of light). The light source can be activated so that just one wavelength of light is active at a given time. One (1), four (4) or other number of photodiode detectors can detect the emitted light of each wavelength after attenuation by the body tissue, such as a finger, toe, ear, nose, hand, foot, forehead, or the like. In an embodiment, four (4) channels correspond to the measured data detected by each of the four (4) photodetectors, and each channel includes the measured data corresponding to each of the eight (8) wavelengths. Thus, raw data representing thirty two (32) signal streams (8 λs×4 detectors) can be generated. Alternatively, the system can use any different number of LEDs, wavelengths, and detectors. For example, the principles described herein apply to a system with 12 LEDs emitting 12 different wavelengths that are measured by 6 detectors. Such a system would generate 72 signal streams of data. Similarly, the principles described herein apply to a system with 6 LEDs emitting 6 different wavelengths of light that are measured by 3 detectors. Such a system would generate 18 signal streams of data.

One or more of the sample waveforms 402 can be selected as acceptable waveforms 406 for conversion to heart sounds. For example, the acceptable waveform 406 may be selected based on waveform characteristics more appropriate for generating audio output, which may be the same, similar to, or even different from waveform characteristics more appropriate for visual output to a patient monitor or continued processing for determining parameter measurements. For example, waveforms may be selected because of their morphology, based on pattern matching, through pulse qualification and detection techniques, or the like. As will be recognized by an artisan from the disclosure herein, the morphology of waveforms, the frequency content of waveforms, or the like may be analyzed to determine the type of waveform characteristics that, when subsequently processed using the disclosure herein, produce heart sounds most similar to the original heart sounds or most beneficial to assist in identifying desired diagnoses or other information from the sounds produced.

In some pulse oximeters, pulse oximeters use noise and other processing to generate or otherwise process the plethysmograph, resulting in cleaner or otherwise more expected plethysmograph waveform shape and data. The waveform samples 402 may be responsive to pre-processed plethysmograph data, semi-processed, or post-processed plethysmograph data. In alternative or in addition to audio parameters, the acceptable waveforms 406 may be selected based on the processing to determine measurement values for physiological parameters. For example, indications of noise in the waveforms, or waveforms associated with high confidence processing techniques may be selected. Also, when parameter processing determines that conditions of improper sensor application or misalignment of the sensor's emitter and detector exist, those corresponding waveforms may be excluded.

In some examples, one or more of the sample waveforms 402 can be processed before selecting the acceptable waveform 406. Any of the techniques described herein or generally known in the art can be used to process the sample waveforms 402. These techniques can be used alone or in combination with each other. As one example, the sample waveforms 402 can be interpolated to create the acceptable waveforms 406. As another example, the sample waveforms 402 can be calibrated by comparing each sample waveform 402 to a calibration curve specific to the heart sound processor. Since each of the sample waveforms 402 may be generated at a different wavelength of light, each of the sample waveforms 402 can be calibrated using a calibration curve to generate an acceptable waveform at a wavelength expected by the heart sound processor.

The terms "calibration curve," "calibration data," and "calibration information" as used herein include the broad ordinary meaning in the pulse oximeter industry that an artisan reviewing this disclosure would recognize, which includes data that maps measured data to often clinically or otherwise determined desired data. For example, in the present disclosure, the calibration curve may include a function, a number of functions, or the like that capture a relationship between waveform information and heart sound signals. The heart sound signals may be measured electronically across a patient population, for an individual patient, or the like.

In yet another example, the sample waveforms 402 can be processed by removing waveforms that do not correspond to acceptable parameters. These parameters can be based at least in part on a waveform acceptable for audio output and/or a physiologically acceptable waveform. Certain waveforms may be discarded if the shape does not meet certain conditions indicative of an acceptable waveform. The pre-determined conditions can include, but are not limited to, the level of curvature, curvature changes, amplitude, position of peaks and valleys, distance between peaks and valleys, and/or slope of line intersecting peaks and valleys. Other processing techniques are disclosed in at least U.S. Pat. No. 6,463,311, which is hereby incorporated by reference in its entirety.

After selecting the one or more acceptable waveforms 406, the sensor can continue collecting data from the streams of data corresponding to the acceptable waveforms 406 and store the corresponding plethysmographs on a storage device, so the clinician can access the acceptable waveforms 406 when necessary. Alternatively, if the pulse oximeter continues to collect data from each data stream, only the acceptable waveforms 406 need to be stored on the storage device.

Next, the acceptable waveforms 406, alone or in combination with white noise 414 generated by, for example, a pseudo-random noise generator (block 412), can be processed using math modeling techniques to create a signal simulating heart sounds 410. Any math modeling technique generally known in the art can be used including, but not limited to, nonlinear inverse modeling.

The modeling can be based at least in part on one or more maps developed for each part of the patient's body. For example, the one or more maps can illustrate the relationship between heart sounds and physiological parameters obtained during clinical trials. The physiological parameters can include information obtained from a plethysmograph. Alternatively, the map can be patient-specific. For example, a clinician can record the sounds from different parts of patient's body using a stethoscope or any other acoustic device. The recordings and the plethysmograph can be used create one or more maps illustrating the relationship between the audio recordings and the patient's plethysmograph from the same time interval.

After developing the heart sound signal 410, the heart sound signal 410 can be input into an audio processor (e.g., codec) 416 to convert the heart sound signal 410 to a heart sound output 418. If the white noise 414 was not included in the heart sound signal 410, then the white noise 414 can be input at this stage.

Figure 4A:
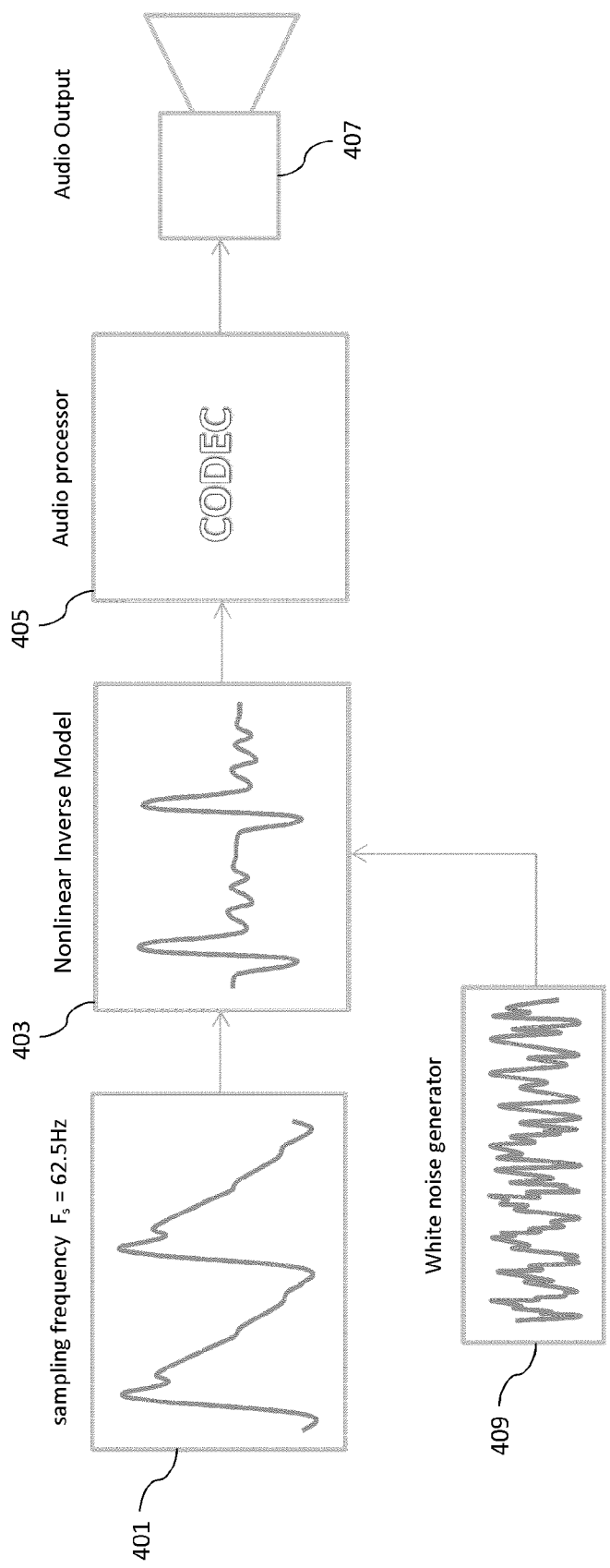
FIG. 4a is another block diagram of an exemplary data flow through one or more signal processors to simulate a heart sound using a plethysmograph waveform.

FIG. 4A is another block diagram of an exemplary data flow through one or more signal processors to simulate a heart sound using a plethysmograph waveform. The method can include collecting one or more sample plethysmograph waveforms at a sampling frequency (block 401). The sampling frequency can be, for example, about 62.5 Hz. Thereafter, a nonlinear inverse model can be used to transform the sample waveforms to a heart sound signal (block 403). The sample waveforms can be at least partially transformed by combination with white noise created by a white noise generator (block 409). Finally, the heart sound signal can then be processed using an audio processor (block 405) to create the heart sound output (block 407).

FIG. 5 illustrates another exemplary data flow 500 converting a plethysmograph to a heart sound output. Similar to the method illustrated in FIG. 4, one or more sample plethysmograph waveforms 502 can be calibrated to select one or more waveforms 506 acceptable for audio output and/or specific physiological parameters (block 504). The sample waveforms 502 can be calibrated using any technique described herein or generally known in the art, including, but not limited to interpolation, comparison with a calibration curve, and/or removal of waveforms based on pre-determined parameters.

The acceptable waveforms 506 can be oversampled at a higher frequency (block 520). For example, the oversampled waveforms 522 can be generated by oversampling the acceptable waveforms 506 at a frequency within the audio band for high fidelity sound. In some embodiments, the oversampling frequency can be at least about 16 Hz and/or less than or equal to about 16 kHz. The oversampling step (block 520) can help improve the resolution of the waveform by generating more data points.

The acceptable waveforms 506 can be oversampled at any frequency within the audio band for high fidelity sound, including, but not limited, any frequency over the sampling frequency that can help improve resolution. In some embodiments, the acceptable waveforms 506 can be oversampled at a frequency that is at least about 50 times and/or less than or equal to about 250 times the frequency at which the waveform samples 502 are collected. In some embodiments, the acceptable waveforms 506 can be oversampled 520 at a frequency that is about 100 times the frequency at which the waveform samples 502 are collected. For example, the waveform samples 502 can be collected at a frequency of 62.5 Hz, while the acceptable waveforms 506 can be oversampled at a frequency of about 6250 Hz.

The oversampling step (block 520) can include collecting data from the pulse oximeter sensor at the oversampling frequency, specifically from the data streams corresponding to the acceptable waveforms 506. Alternatively, the oversampled waveforms 522 can be generated using other techniques generally known in the art such as interpolation. The oversampled waveforms 522 can be stored on a storage device and recalled when necessary.

After generating the oversampled waveforms 522, the oversampled waveforms 522 can be processed using math modeling techniques generally known in the art (block 508), including, but not limited to, a linear inverse model or a nonlinear inverse model to transform the waveforms 522 to heart sound signals 510. In some examples, both the oversampled waveforms 522 and white noise 514 can be processed together to create the heart sound signal 510. In other examples, as illustrated in FIG. 5, only the oversampled waveform 522 is transformed into the heart sound signal 510. In the latter example, a linear inverse model may be particularly appropriate because of the simplified inputs.

As described in connection with FIG. 4, the basis for the math modeling can be one or more maps illustrating the relationship between physiological parameters (e.g., plethysmographs) obtained during clinical trials and heart sounds. Multiple maps representative of heart sounds from different parts of the patient's body can be created. For example, a clinician can record the sounds from different parts of patient's body using a stethoscope or any other acoustic device and store the patient's plethysmograph from the same time interval. These sound recordings and the plethysmograph can be used to create the one or more maps illustrating the relationship between the plethysmograph and the different heart sounds. The one or more maps can be developed from clinical data or specifically derived from each patient.

The method also includes generating white noise (block 512) and processing the white noise 514 together with the oversampled waveforms 522 or heart sound signal 510. In some examples, the white noise 514 can be passed through a band pass filter to select one or more tones corresponding to a natural heart sound (block 524). The natural heart tones include tones that clinicians are trained to expect when examining the patient with a stethoscope. As shown in FIG. 5, an audio processor processes the heart sound tones 526 together with the heart sound signal 510 to generate a heart sound output 518 (block 516).

Figure 5A:
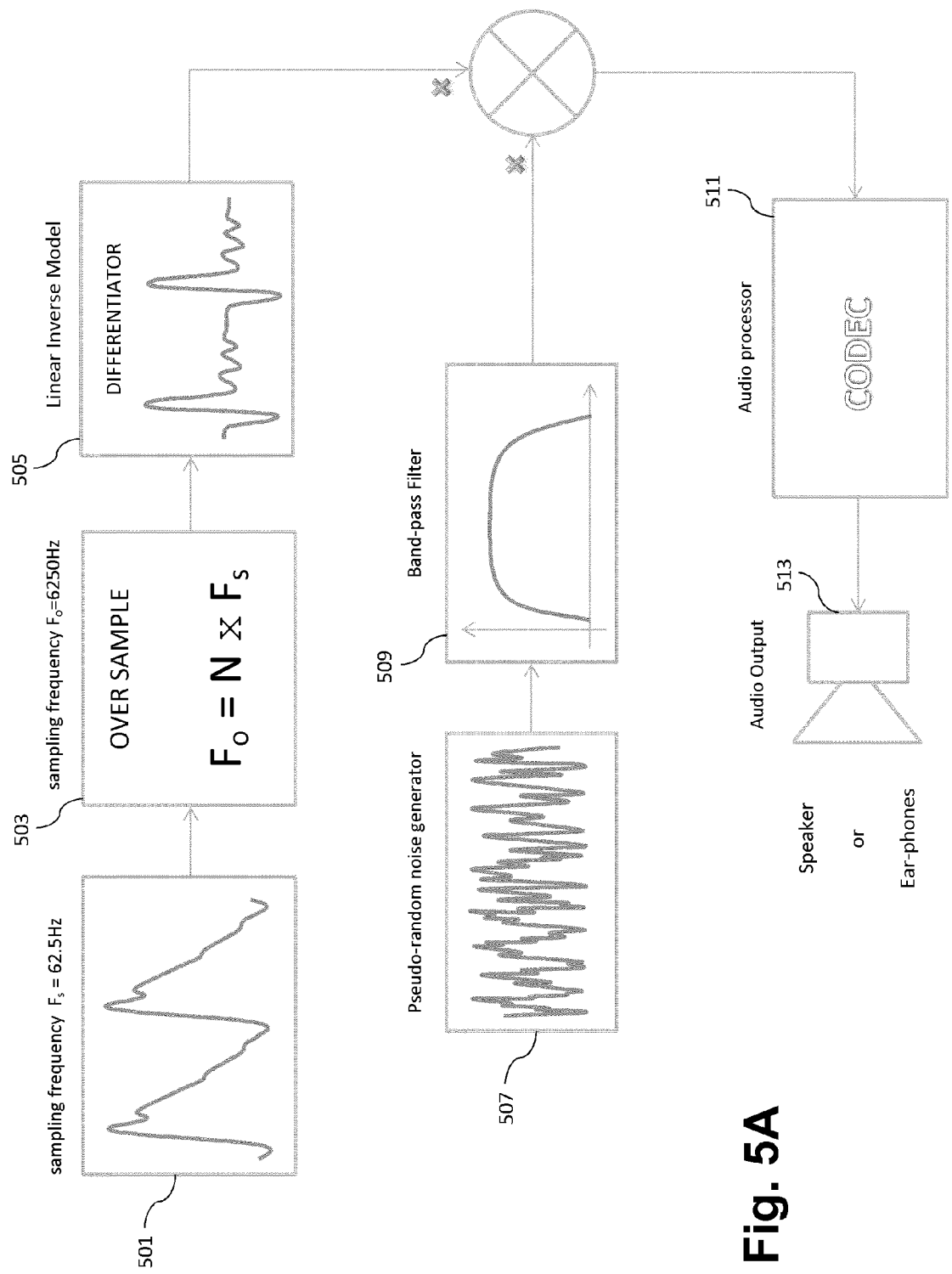
FIG. 5a is another block diagram of another exemplary data flow through one or more signal processors to simulate a heart sound using a plethysmograph waveform.

FIG. 5A is another block diagram of an exemplary data flow through one or more signal processors to simulate a heart sound using a plethysmograph waveform. The method can include collecting one or more sample plethysmograph waveforms at a sampling frequency (block 501), which, in some examples, can be about 62.5 Hz. The sample waveforms can then be oversampled at an oversampling frequency (block 503), which, in some examples, can be about 6250 Hz. After the oversampling step, a linear inverse model can be used to transform the over-sampled waveforms to a heart sound signal (block 505).

A pseudo-random noise generator can create white noise (block 507), which can be band-pass filtered for specific tones (block 509), including, but not limited to, specific tones corresponding to tones clinicians are trained to hear from a stethoscope. Thereafter, the filtered noise can be combined with the heart sound signal and processed using an audio processor (block 511) to create the heart sound output (block 513).

Figure 6:
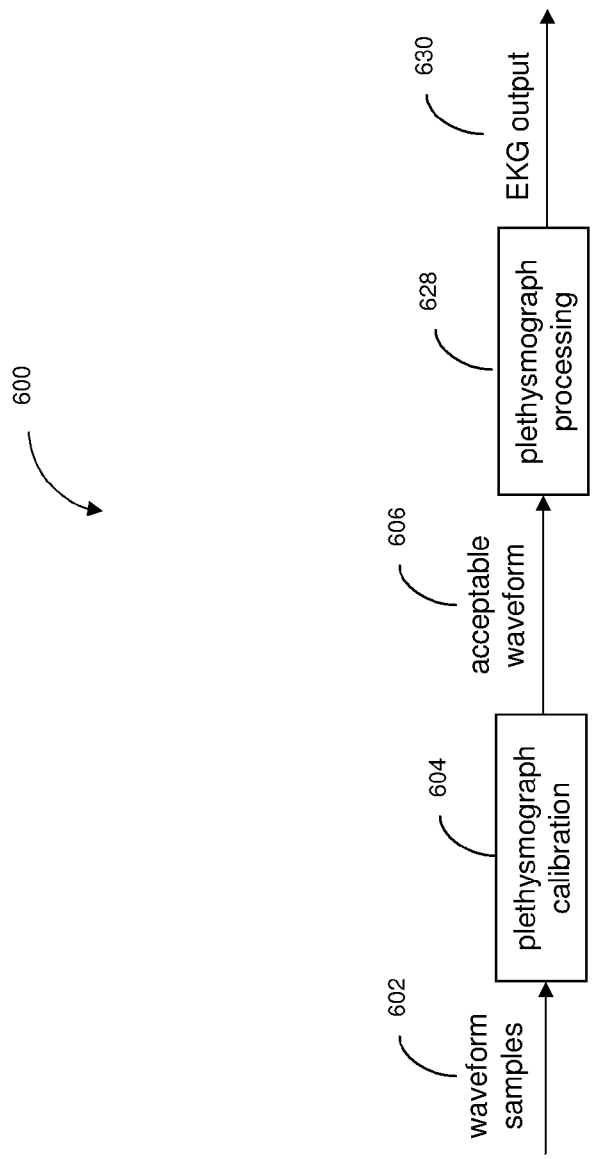
FIG. 6 is a block diagram of an exemplary data flow through one or more signal processors to transform a plethysmograph waveform to an EKG waveform.

FIG. 6 illustrates a data flow 600 to convert a plethysmograph to an EKG output. Ordinarily, an EKG sensor includes one or more leads attached to different points on the patient's body. Using the data flow 600 illustrated in FIG. 6, the EKG simulator can advantageously reduce the total number of sensors and cables that need to be attached to the patient.

Similar to the previously described examples, multiple plethysmograph samples 602 can be calibrated to select one or more acceptable waveforms 606 according to certain parameters (block 604). These parameters can be based at least in part on appropriate physiological parameters and/or data necessary for an adequate EKG output. The sample waveforms 602 can be calibrated using any technique described herein or generally known in the art, including, but not limited to interpolation, comparison with a calibration curve, and/or removal of waveforms based on predetermined parameters. These techniques can be used alone or in combination with each other.

After selecting the acceptable waveforms 606, the pulse oximeter can continue to collect data exclusively the data streams corresponding to the acceptable waveforms 606 and store the acceptable waveforms 606 on a storage device. If the pulse oximeter continues to collect data from all of the data streams, then only the waveforms from the data streams corresponding to the acceptable waveforms 606 need to be stored.

Although not illustrated in FIG. 6, in some examples, the acceptable waveforms 606 can be oversampled to improve resolution or decrease noise. Any oversampling technique described herein or generally known in the art can be used. For example, the pulse oximeter can simply collect data at a higher frequency or interpolation techniques can be used to oversample the data.

After selecting the acceptable waveforms 606, the processor can convert the acceptable waveforms to an EKG output 630 using any math modeling technique generally known in the art (block 628), including, but not limited to a nonlinear inverse model or a linear inverse model. The basis for the modeling can be one or more maps derived from clinical studies or the patient's own data. For example, a clinician can store the patient's plethysmograph and EKG output from the same time interval, and these recordings can be used to create a map illustrating the relationship between the EKG output and the plethysmograph. Later generated plethysmographs can be entered into a model based on these one or more maps to simulate the patient's EKG output.

Figure 6A:
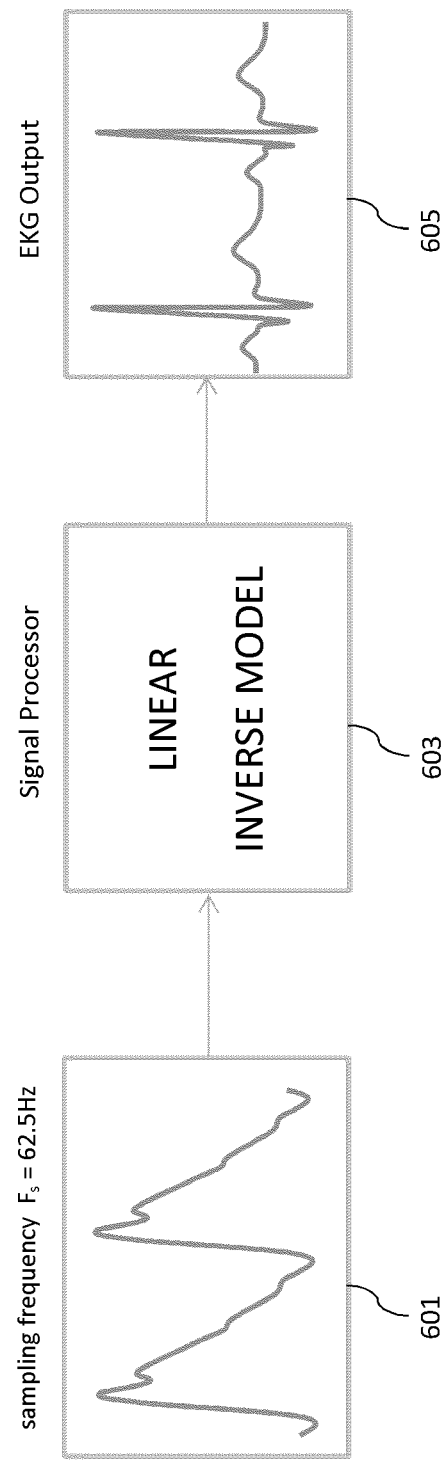
FIG. 6a is another block diagram of an exemplary data flow through one or more signal processors to transform a plethysmograph waveform to an EKG waveform.

FIG. 6A is another block diagram of an exemplary data flow through one or more signal processors to transform a plethysmograph waveform to an EKG output. The method can include collecting one or more sample plethysmograph waveforms at a sampling frequency (block 601). The sampling frequency can be, for example, about 62.5 Hz. Thereafter, a linear inverse model (block 603) can be used to transform the waveform samples into the EKG output (block 605).

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor can also include primarily analog components. For example, any of the signal processing algorithms described herein can be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A heart sound simulator configured to determine heart sounds from photo-plethysmograph data, the heart sound simulator comprising:
   an optical sensor configured to detect an attenuation of light by body tissue, the optical sensor being further configured to generate a signal based on the detected attenuation, said optical sensor including a light source and light detector;
   a processor configured to receive the generated signal, said processor configured to:
   process the received signal to determine a plurality of plethysmograph waveforms,
   analyze the plurality of plethysmograph waveforms to determine a subset of the plurality of plethysmograph waveforms that have a first waveform characteristic, wherein a plethysmograph waveform in the plurality of plethysmograph waveforms that has the first waveform characteristic is more appropriate for generating audio output than another plethysmograph waveform in the plurality of plethysmograph waveforms that does not have the first waveform characteristic, and
   output a heart sound signal based on the subset of the plurality of plethysmograph waveforms;

a noise generator configured to generate white noise; and
a filter configured to filter the white noise to form filtered noise that represents one or more heart tones, and
wherein the processor is further configured to combine the heart sound signal and the filtered noise to generate a heart sound output.

2. The heart sound simulator of claim 1, wherein the processor is further configured to use calibration information to determine the heart sound signal.

3. The heart sound simulator of claim 1, wherein the processor is further configured to oversample said subset of the plurality of plethysmograph waveforms.

4. The heart sound simulator of claim 3, wherein said subset of the plurality of plethysmograph waveforms include a first frequency and wherein said processor is further configured to oversample said subset of the plurality of plethysmograph waveforms at a second frequency higher than the first frequency, wherein the second frequency is at least about 100 times the first frequency.

5. The heart sound simulator of claim 1, wherein said processor is configured to output the heart sound output in an audio format.

6. The heart sound simulator of claim 1, further comprising a memory configured to store the generated signal, wherein said processor is further configured to receive the generated signal stored on the memory.

7. The heart sound simulator of claim 6, wherein said processor is further configured to determine whether the generated signal includes an abnormal value.

8. The heart sound simulator of claim 7, wherein the processor is further configured to determine whether said abnormal value falls within a first the time window.

9. The heart sound simulator of claim 1, wherein the one or more heart tones comprises one or more natural heart tones.

10. The heart sound simulator of claim 1, wherein the first waveform characteristic comprises at least one of a waveform morphology or a waveform frequency content.

11. A method of simulating heart sounds using one or more plethysmograph signals responsive to light attenuated by body tissue detected by an optical sensor in proximity to a measurement site, the method comprising:

receiving, at a signal processor, signals generated by the optical sensor, wherein the signals are generated in response to detecting light attenuated by body tissue;
identifying a plurality of plethysmograph waveforms using said signal processor;
analyzing the plurality of plethysmograph waveforms to determine a subset of the plurality of plethysmograph waveforms that have a first waveform characteristic, wherein a plethysmograph waveform in the plurality of plethysmograph waveforms that has the first waveform characteristic is more appropriate for generating audio output than another plethysmograph waveform in the plurality of plethysmograph waveforms that does not have the first waveform characteristic;
electronically generating a heart sound signal based on the subset of the plurality of plethysmograph waveforms using said signal processor;
generating white noise;
filtering the white noise to form filtered noise that represents one or more heart tones; and
combining the heart sound signal and the filtered noise to generate a heart sound output.

12. The method of claim 11, wherein said generating the heart sound signal comprises generating an audio signal that simulates heart sounds.

13. The method of claim 11, wherein identifying the subset of the plurality of plethysmograph waveforms comprises sampling a plurality of signal streams at a first frequency.

14. The method of claim 13, further comprising oversampling the subset of the plurality of plethysmograph waveforms at a second frequency higher than the first frequency.

15. The method of claim 14, wherein the second frequency is at least about 100 times the first frequency.

16. The method of claim 11, wherein generating the heart sound signal comprises transforming the subset of the plurality of plethysmograph waveforms using modeling techniques.

17. The method of claim 11, further comprising outputting the heart sound output in an audio format.

18. The method of claim 11, wherein the one or more heart tones comprises one or more natural heart tones.

* * * * *